United States Patent
Kavanagh

(10) Patent No.: US 11,039,866 B2
(45) Date of Patent: Jun. 22, 2021

(54) BONE SCREW WITH 3D PRINTED THREAD LOCKING FEATURE

(71) Applicant: ETHICON LLC, Guaynabo, PR (US)

(72) Inventor: Edward P. Kavanagh, Mallow (IE)

(73) Assignee: Cilag GmbH International, Zug (CH)

( * ) Notice: Subject to any disclaimer, the term of this patent is extended or adjusted under 35 U.S.C. 154(b) by 212 days.

(21) Appl. No.: 16/182,829

(22) Filed: Nov. 7, 2018

(65) Prior Publication Data
US 2020/0138492 A1 May 7, 2020

(51) Int. Cl.
*A61B 17/80* (2006.01)
*A61B 17/86* (2006.01)
*A61B 17/74* (2006.01)

(52) U.S. Cl.
CPC ...... *A61B 17/8057* (2013.01); *A61B 17/8052* (2013.01); *A61B 17/863* (2013.01); *A61B 17/74* (2013.01)

(58) Field of Classification Search
CPC ............ A61B 17/8033; A61B 17/8047; A61B 17/8057
See application file for complete search history.

(56) References Cited

U.S. PATENT DOCUMENTS

| | | | |
|---|---|---|---|
| 6,974,461 B1 * | 12/2005 | Wolter | A61B 17/80 606/283 |
| 9,404,525 B2 * | 8/2016 | Arnett | A61B 17/8057 |
| 10,383,668 B2 | 8/2019 | Rutledge et al. | |
| 2011/0224737 A1 * | 9/2011 | Lewis | A61B 17/861 606/290 |
| 2011/0288598 A1 * | 11/2011 | Moed | A61B 17/8625 606/303 |
| 2012/0083847 A1 * | 4/2012 | Huebner | A61B 17/8057 606/281 |
| 2014/0330320 A1 | 11/2014 | Wolter | |
| 2017/0231673 A1 | 8/2017 | Hirata et al. | |
| 2019/0328430 A1 * | 10/2019 | Bosshard | A61B 17/8057 |

FOREIGN PATENT DOCUMENTS

EP 2 614 787 A1 7/2013

OTHER PUBLICATIONS

European Search Report and Written Opinion dated Mar. 24, 2020 for Application No. EP 19207775.8, 11 pgs.

* cited by examiner

*Primary Examiner* — Nicholas W Woodall
(74) *Attorney, Agent, or Firm* — Frost Brown Todd LLC

(57) ABSTRACT

A bone screw assembly includes a first body, a second body, and a thread locking assembly that may couple the first body with the second body. The first body includes a proximal portion, a distal portion that may pierce bone in response to rotation of the first body about the longitudinal axis, and a first threaded section that may engage bone. The second body defines a through hole that may receive the distal portion of the first body. The thread locking assembly includes a first thread locking section associated with the proximal portion of the first body, and a second thread locking section associated with the through hole of the second body. Either the first threaded locking section or the second threaded locking section deforms the other in response to rotation of the first threaded locking section relative to the second threaded locking section.

18 Claims, 8 Drawing Sheets

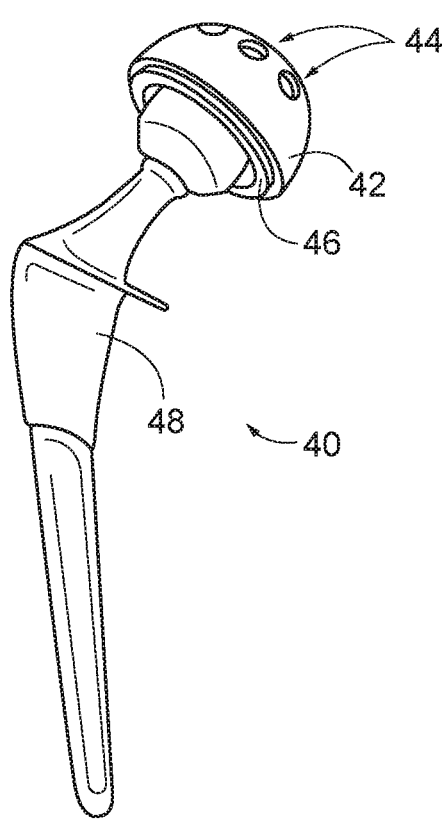
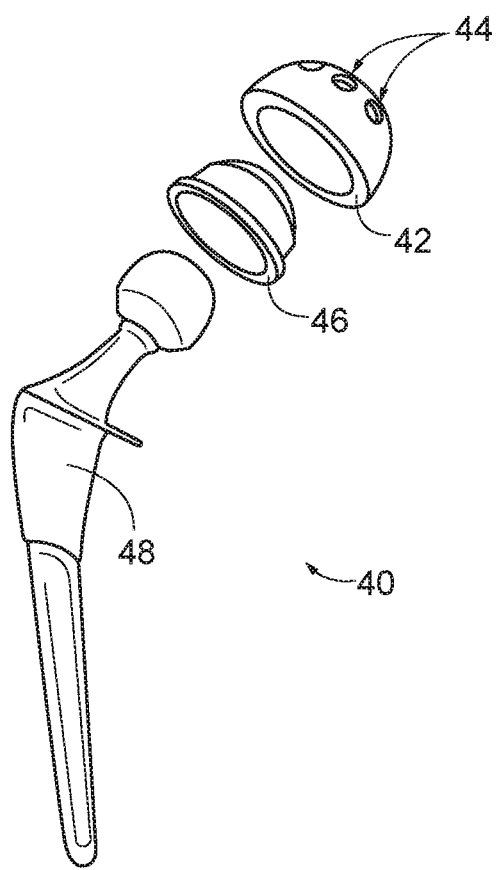
FIG. 2
FIG. 3

BONE SCREW WITH 3D PRINTED THREAD LOCKING FEATURE

BACKGROUND

Medical screws or orthopedic (bone) screws may be used in orthopedic procedures to help immobilize bone segments of a fractured bone to promote healing. In some instances, bone screws are used in conjunction with a bone plate to help further immobilize segments of fractured bones. In some other instances, bone screws may be used to attach a prosthesis to a bone, such as an acetabular component of a hip joint replacement prosthesis or a tibia component of a total knee replacement prosthesis. Once the bone screw is deployed, it may be desirable to ensure that the bone screw remains suitably secured to its surroundings. Therefore, a bone screw may be configured to engage and secure to both a bone, and, if present, a bone plate or other prosthesis component. Bone screws may have multiple threaded regions configured to engage different elements. In such instances, one threaded region may be configured to engage and couple with a bone, while a second threaded region may be configured to engage and couple with a complementary threading located on the bone plate or other prosthesis.

Three-dimensional (3D) printing is an additive printing process used to make three-dimensional solid objects from a digital model. 3D printing may be used in various processes including but not limited to rapid product prototyping, product manufacturing, mold generation, and mold master generation. 3D printing techniques are considered additive processes because they involve the application of successive layers of material. This is unlike traditional machining processes, which often rely upon the removal of material to create the final object. Various materials may be used in 3D printing. For example, materials such as polymide, alumide, titanium, or thermoplastic polyurethane may be used in 3D printing. Some 3D printing techniques utilize powder as the basic material, then transform the powder into a desired shape or structures to form a product. For example, laser sintering involves applying successive thin layers of powder, one layer on top of the next. Between application of each layer of powder, a laser travels over desired portions of the current powder layer and sinters targeted powder together, eventually forming the desired shape or structure. Once complete, the final product may be removed from the unsintered powder.

While various kinds of bone screws and bone plates have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2 depicts a perspective view of an exemplary hip replacement prosthesis;

FIG. 3 depicts an exploded perspective view of the exemplary hip replacement prosthesis of FIG. 2;

Figure 1:
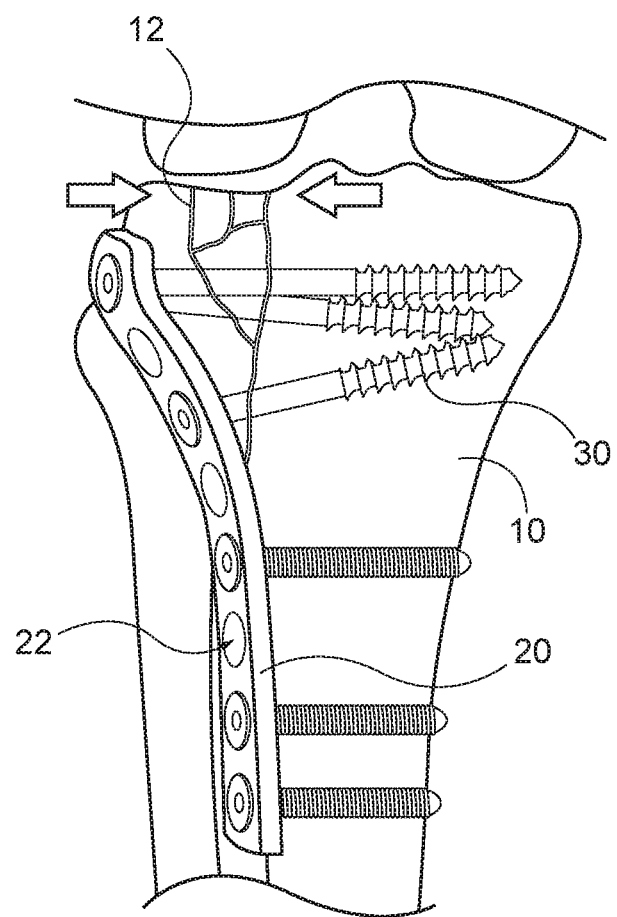
FIG. 1 depicts an elevational side view of a bone plate attached a bone via bone screws to immobilize fracture segments of the bone, where the bone is transparent for purposes of clarity.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Bone Screws and Bone Plates

As mentioned above, bone screws may be used to immobilize fragments of fractured bones, attach various prostheses to corresponding anatomy, or for any other suitable purposes as would be apparent to one having ordinary skill in the art in view of the teachings herein. In some instances, bone screws may be used by themselves to immobilize and help heal fractures. However, in other instances bone screws may be used in conjunction with a bone plate or other structure to provide additional structural support.

FIG. 1 shows the use of a plurality of bone screws (30) in conjunction with a bone plate (20) to immobilize fractures (12) on a bone (10). Bone plate (20) is dimensioned to abut against or extend along the profile of the exterior surface of bone (10). Bone plate (20) may be used in conjunction with bone screws (30) to provide structural support for bone (10). It should be understood that different anatomical locations demand different shapes and sizes of bone plates (20). Therefore, bone plate (20) may have any suitable shape, size, and/or profile configured to engage a corresponding anatomical structure of bone (10) as would be apparent to one having ordinary skill in the art in view of the teachings herein. For example, bone plate (20) may be dimensioned for use on the jaw, on the pelvis, on the forearm, and/or around joints of a patient. Similarly, bone screw (30) may have any suitable shape, size, and/or profile as needed.

Figure 5:
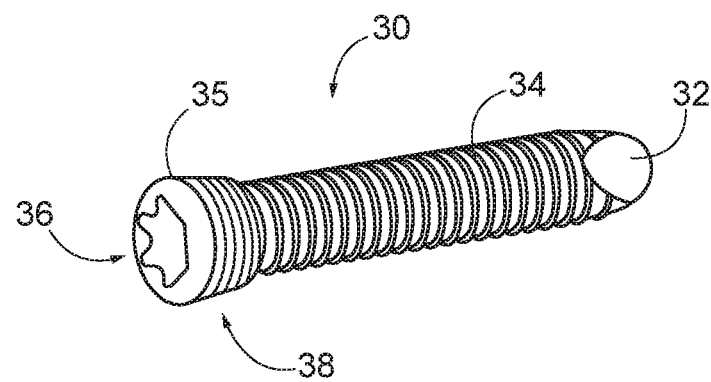
FIG. 5 depicts a perspective view of an exemplary bone screw.

As best seen in FIG. 5, an exemplary bone screw (30) includes self-tapping flutes (32) at the distal end, a first threaded portion (34), and head (35). Self-tapping flutes (32) are dimensioned and configured to penetrate and drive into bone (10) in response to rotation of bone screw (30) about its own longitudinal axis. First threaded portion (34) is configured to further engage bone (10) as bone screw (30) is driven about its own longitudinal axis. In particular, first threaded portion (34) is configured to engage bone (10) in order to help fix screw (30) relative to bone (10) when bone screw (30) is suitably deployed.

Figure 6:
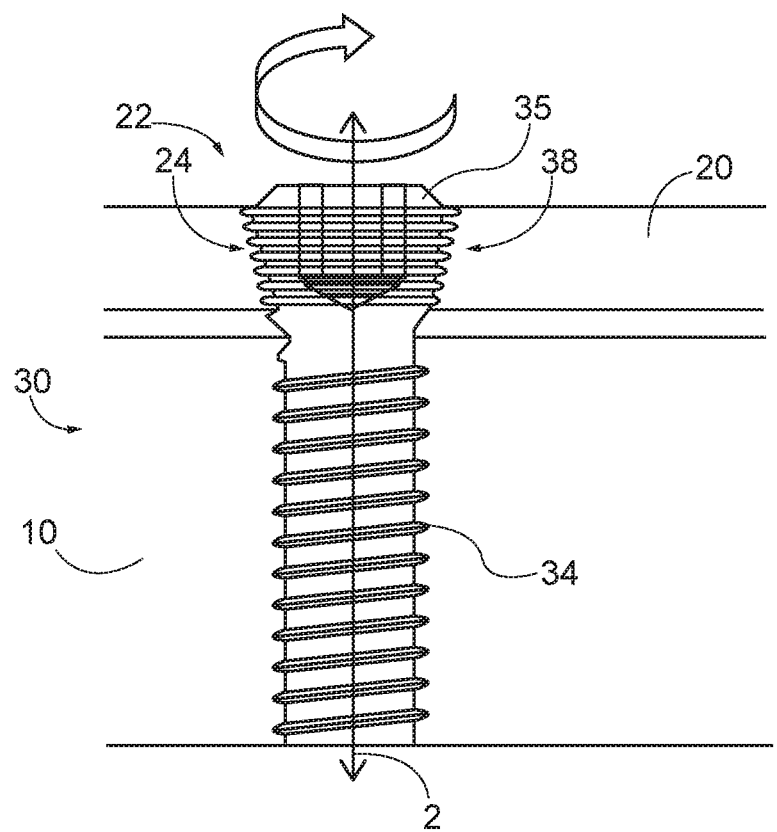
FIG. 6 depicts a cross-sectional front view of the bone screw of FIG. 5 attached to the bone plate of FIG. 1.

Head (35) includes a locking threaded portion (38). As best seen in FIG. 6, when bone screw (30) is suitably coupled with bone (10) and bone plate (20), locking threaded portion (38) may suitably mesh with internal female threading (24) of bone plate (20) in order to help fixate bone screw (30) relative to bone plate (20). Because bone screw (30) includes first threaded portion (34) configured to help fixate bone screw (30) relative to bone (10), and because bone screw (30) includes locking threaded portion (38) configured to help bone screw (30) fixate to bone plate (20), bone screw (30) may be used to help fixate bone plate (20) relative to bone (10). The threaded coupling between bone screw (30) and bone plate (20) allows bone screw (30) to couple with bone plate (20) at a suitable torque value. In other words, bone screw (30) may couple or decouple with bone plate (20) when bone screw (30) and/or bone plate (20) are torqued about the longitudinal axis of threading at the suitable torque value.

Head (35) also defines a drive recess (36). Drive recess (36) is dimensioned to couple with a driving tool (e.g., screwdriver, driving key, etc.) that may rotate bone screw (30) about its own longitudinal axis. Therefore, a driving tool may engage bone screw (30) at drive recess (36) in order to suitably torque bone screw (30) about its own longitudinal axis in accordance with the description herein. Drive recess (36) may allow the suitable torque required to couple bone screw (30) with bone plate (20) via threading (24, 38) to be increased, which may lead to a greater coupling strength.

As mentioned above, bone plate (20) may be affixed to bone (10) by bone screws (30). In particular, various bone screws (30) may be inserted into corresponding through holes (22) defined by bone plate (20). Bone screws (30) may then be driven into engagement with bone (10) until a head (35) of bone screws (30) meshes with bone plate (20) in accordance with the description herein. As best seen in FIG. 1, bone screws (30) may also extend through fractures (12) of bone (10) to also help immobilize bone (10). Therefore, bone plate (20) and bone screws (30) may help stabilize fractures (12) of bone (10) relative to each other, while bone plate (20) may help provide additional structural support.

Figure 4:
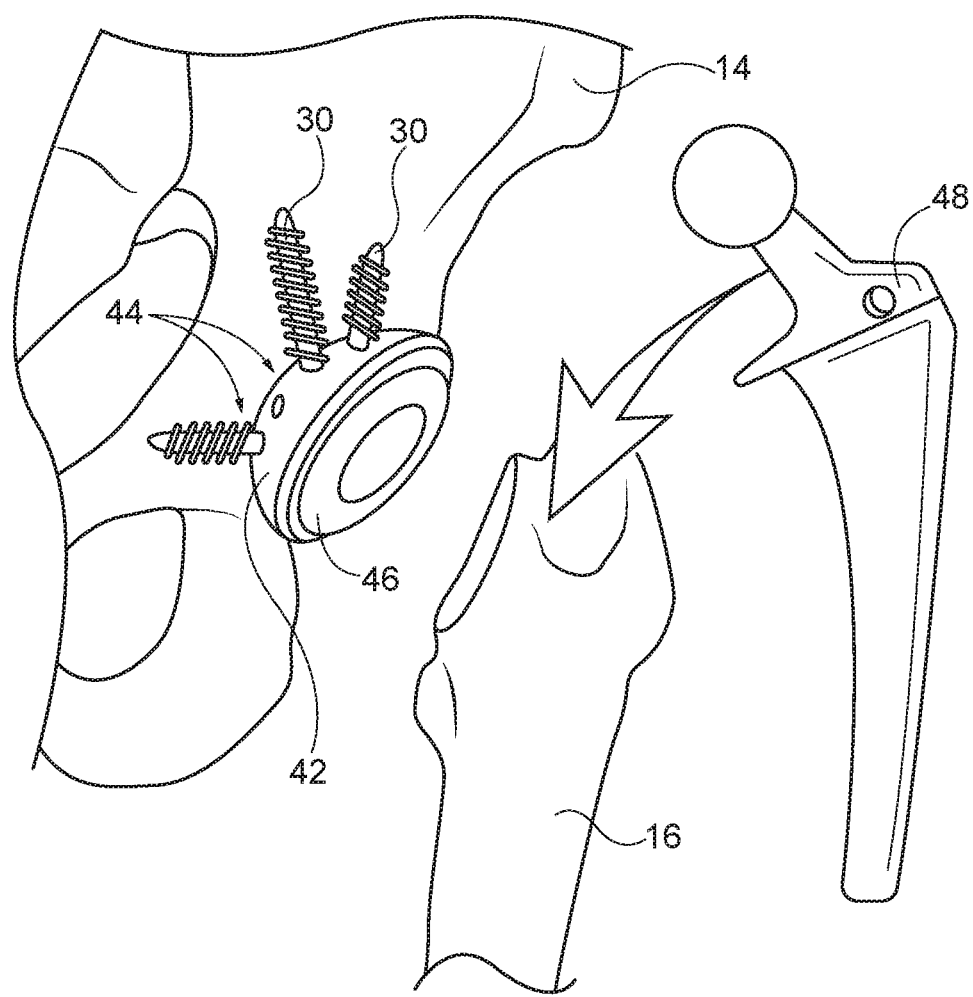
FIG. 4 depicts a partially exploded perspective view of the hip replacement prosthesis of FIG. 2 partially attached to a patient.

As mentioned above, bone screws (30) may also be used to attach certain prosthesis implants to bones. FIGS. 2-3 show an exemplary hip replacement prosthesis (40) including an acetabular component (42) defining threaded through holes (44), a plastic liner (46), and a femoral component (48). As shown in FIG. 4, acetabular component (42) of hip replacement prosthesis (40) may be affixed to pelvis (14) by bone screws (30). In particular, bone screws (30) may be inserted through threaded through holes (44) defined by the internal cavity of acetabular component (42). Bone screws (30) may then be driven into engagement with pelvis (14) until head (35) of bone screws (30) engage threaded through holes (44). Threaded through holes (44) may have internal female threading substantially similar to threading (24) described above for bone plate (20). Therefore, bone screw (30) may affix to pelvis (14) via first threaded portion (34), while bone screw (30) may also affix to acetabular component (42) via locking threaded portion (38) and threaded through holes (44). In other words, bone screws (30) may help fixate acetabular component (42) to pelvis (14).

When suitably implanted, femoral component (48) may move relative to acetabular component (42). Additionally, when suitably implanted, femoral component (48) and acetabular component (42) may transfer loads between each other. Therefore, bone screws (30) may help keep acetabular component (42) fixed relative to pelvis (14) in order to accommodate movement, as well as weight transfers between femoral component (48) and acetabular component (42).

It should be understood that acetabular component (42) is just one exemplary prosthesis that bone screw (30) may be used in conjunction with. Bone screw (30) may be used with any other suitable exemplary prostheses having threaded through holes as would be apparent to one having ordinary skill in the art in view of the teachings herein. For instance, bone screws (30) may be utilized to fixate a tibia prosthesis component during a total knee replacement.

II. Alternative Exemplary Bone Screws and Bone Plates

The term "bone plate" should be interpreted as any structural body that may couple with any suitable anatomy via a bone screw (30). Therefore, as used herein, the term "bone plate" may include various prosthesis components configured to couple with a bone, such as a tibia prosthesis component of a total knee replacement, an acetabular component of a hip replacement, etc.

As mentioned above, while first threaded portion (34) may engage bone (10) to fixate bone screw (30) with bone (10), locking threaded portion (38) may suitably mesh with internal female threading (24) of bone plate (20) in order to help fixate bone screw (30) relative to bone plate (20). As also mentioned above, bone screw (30) may couple or decouple with threaded through holes (22) when bone screws (30) are torqued relative to bone plate (20) about the longitudinal axis of threading at the suitable torque value.

Once bone screw (30) is suitably coupled with bone plate (20) such that bone plate (20) is affixed relative to bone (10), it may be desirable to keep bone screws (30) suitably secured to bone plate (20). However, in some instances, the engagement between internal female threading (24) of bone plate (20) and locking threaded portion (38) of bone screw (30) may eventually loosen. If engagement between internal female threading (24) and locking threaded portion (38) loosens, bone plate (20) may no longer be fixated relative to bone (10). It may therefore be desirable to prevent bone screws (30) from disassociating with bone plate (20) once suitably coupled with each other.

FIGS. 7A-7D show an alternative bone screw (130) and an alternative bone plate (60) that may be configured to prevent bone screw (130) from disassociating with bone plate (60) once suitably coupled with each other. Bone screw (130) and bone plate (60) may be used in replacement of bone screw (30) and bone plate (20) described above.

Therefore, bone screw (130) may be substantially similar to bone screw (30) described above, while bone plate (60) may be substantially similar to bone plate (20) described above, except for the differences described below.

Bone screw (130) includes self-tapping flutes (132) at the distal end, a first threaded portion (134), and head (135), which are substantially similar to self-tapping flutes (32), first threaded portion (34), and head (35) described above, with differences elaborated below. Therefore, self-tapping flutes (132) are dimensioned and configured to penetrate and drive into bone (10) in response to rotation of bone screw (130) about its own longitudinal axis (LA). First threaded portion (134) is configured to further engage bone (10) as bone screw (130) is driven about its own longitudinal axis. In particular, first threaded portion (134) is configured to engage bone (10) in order to help fix bone screw (130) relative to bone (10) when bone screw (130) is suitably deployed.

Head (135) is substantially similar to head (35) described above, with differences elaborated below. Therefore, head (135) defines a drive recess (not shown) that is substantially similar to drive recess (36) describe above. Head (135) also includes a deformable locking threaded portion (138), which may be similar to locking threaded portion (38), with differences elaborated below. Deformable locking threaded portion (138) is operable to conform to an irregular female threading (64) of bone plate (60) when a suitable torque is applied to bone screw (130) about the longitudinal axis (LA). As deformable locking threaded portion (138) of bone screw (130) deforms, this may help the meshed threading (138, 64) between bone screw (130) and bone plate (60) "bind up," lock, jam, or seize up, thereby requiring a large amount of torque to unscrew deformable locking threaded portion (138) out of irregular female threading (64) of bone plate (60). Seizing, locking, jamming, or binding up of threading (138, 64) may ultimately prevent bone screw (130) from disassociating with bone plate (60) once the two are suitably coupled with each other in accordance with the description herein. Deformable locking threaded portion (138) may be made out of any suitable material as would be apparent to one having ordinary skill in that art in view of the teachings herein. Deformation of locking threaded portion (138) may be elastic or plastic.

Bone plate (60) includes at least one threaded through hole (62), each defining an irregular female threading (64). Unlike conventional bone plates (20) that have female threading (24) formed from a conventional tapping machine that removes material to form threading (24) in a pure helical configuration, bone plate (60) may be formed from an additive process like 3D printing. Therefore, female threading (64) may be formed by adding layers of material on top of each other incrementally, rather than using a tapping machine that needs to be removed from through hole (62) after forming female threading (64). It should be understood that the female threading (64) described herein may not be subject to formation via conventional tapping processes, due to the presence of intentional structural irregularities in female threading (64) as described herein.

Irregular female threading (64) has a first female threading portion (70), which connects distally into a second female threading portion (74), which also connects distally into a third female threading portion (80). As will be elaborated below, while female threading portions (70, 74, 80) are continuously connected with each other, female threading portions (70, 74, 80) are not uniform in nature. In other words, if a male threaded member were dimensioned to rotate through first female threading portion (70) in a substantially unimpeded fashion, that same male threaded member would need to be rotated with enough torque to deform itself in order to traverse across second female threading portion (74) and third female threading portion (80).

Therefore, irregular female threading (64) in not axisymmetric about the longitudinal axis (LA) of bone screw (130) when bone plate (60) and bone screw (130) are suitably coupled. In other words, if irregular female threading (64) were viewed from within the confines of threaded through hole (62) at a location along the longitudinal axis (LA) and female threading (64) was rotated, the appearance of female threading (64) would not appear unchanged. Irregular female threading (64) may have deviations in pitch, may have deviations in helix angles, may have deviations in thread angles, may have deviations in root/crest, and may have any other suitable deviations that would leave to deformation of deformable locking threaded portion (138) as would be apparent to one having ordinary skill in the art in view of the teachings herein.

A portion of first female threading portion (70) extends along a first axis (94), but also includes a non-uniform wave (72), thereby creating a substantial non-uniform deviation in helix angle. Similarly, a portion of second female threading portion (74) extends along a second axis (96), but also includes a non-uniform wave (76), thereby creating a substantial non-uniform deviation in helix angle. Likewise, a portion of third female threading portion (80) extends along a third axis (98), but also includes a non-uniform wave (82), thereby creating a substantial non-uniform deviation in helix angle. First axis (94) and second axis (96) define a first angle (100) while second axis (96) and third axis (98) define a second, different angle (102). Similarly, first female threading portion (70) and second female threading portion (74) define a first pitch (90), while second female threading portion (74) and third female threading portion (80) define a second, different, pitch (92). First female threading portions (70), second female threading portion (74), and third female threading portion (80) have deviations in thread angles; and may have deviations in root/crest.

Waves (72, 76, 82), change in pitches (90, 92), and change in angles (100, 102) may interact with deformable locking threaded portion (138) such that once deformable locking threaded portion (138) encounters a wave (72, 76, 82), change in pitch (90, 92), or change in angle (100, 102), the operator must apply enough toque to bone screw (130) about longitudinal axis (LA) in order to deform locking threaded portion (138) of bone screw (130) such that male locking threaded portion (138) may further traverse irregular female threading (64). Once bone screw (130) is fully coupled with bone plate (60), the deformation of deformable male locking threaded portion (138) may conform to the shape of irregular female threading (64). In other words, male locking threaded portion (138) will have a complementary threaded profile as irregular female threading (64). After being suitably coupled, if for some reason bone screw (130) attempts to unscrew or otherwise loosen from bone plate (60), the irregular profile of both female threading (64) and male locking threaded portion (138) will resist rotation of male locking threaded portion (138) out of female threading (64) unless the rotation has enough torque to re-deform or damage male locking threaded portion (138). This resistance to rotation may help prevent bone screws (130) from disassociating with bone plate (60) once suitably coupled with each other.

In the current example, male locking threaded portion (138) is deformable, while female threading (64) is irregular.

However, this is merely optional. In another example, male locking threaded portion (138) may be irregular, while female threading (64) may be deformable such that insertion of male locking threaded portion (138) deforms female threading (64). Of course, both male threading (138) and female threading (64) may have irregularities that in turn deform each other during coupling. In some variations, irregular female threading (64) may slightly deform while male threading (138) may not deform at all. In such cases, the deforming irregularities of female threading (64) may provide interferences with the non-deforming regular male threading (138), thereby effectively locking the threads together through an interference fit.

In the current example, bone plate (60) is entirely 3D printed while forming irregular female threading (64). However, this is merely optional. For instance, bone plate (60) may start as regular plate with larger screw holes preformed. Then, irregularities of female threading (64) may be subsequently added via the additive process of 3D printing. OF course, irregularities of female threading (64) may be formed utilizing any other suitably means as would be apparent to one having ordinary skill in the art in view of the teachings herein.

Figure 7A:
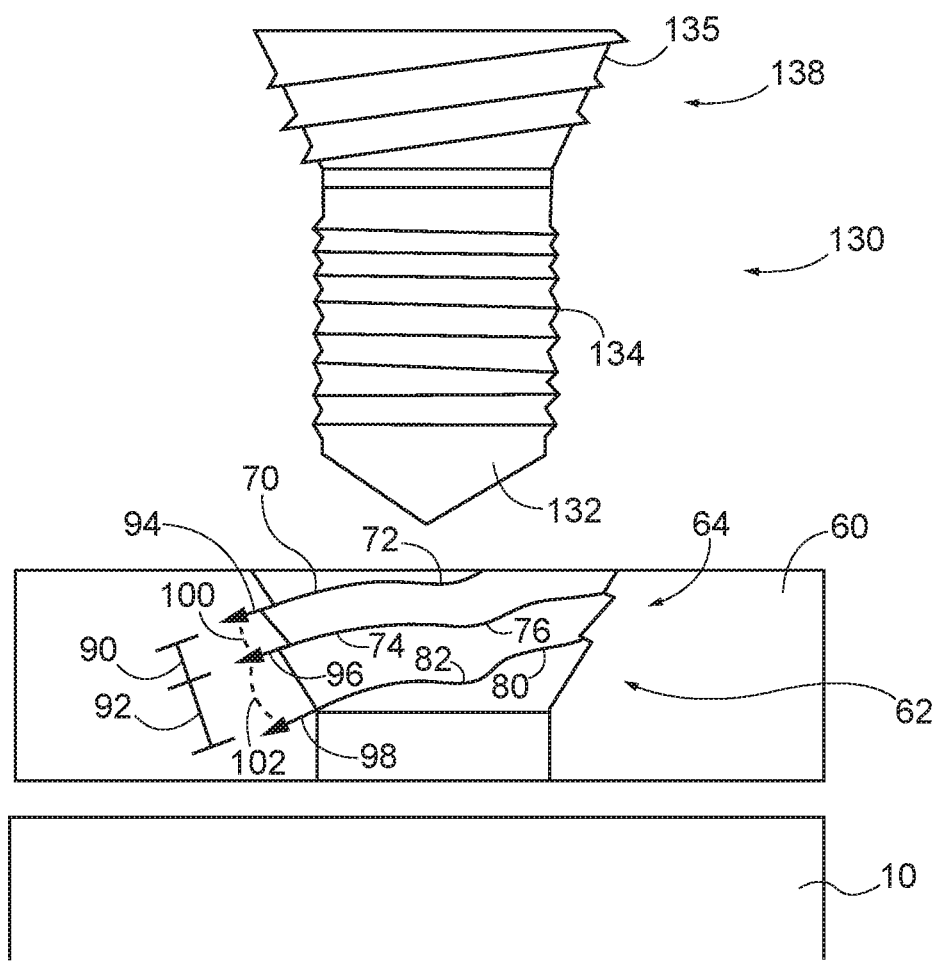
FIG. 7A depicts a cross-sectional front view of an alternative bone screw aligned for coupling with an alternative bone plate attached to the bone of FIG. 1.
Figure 7B:
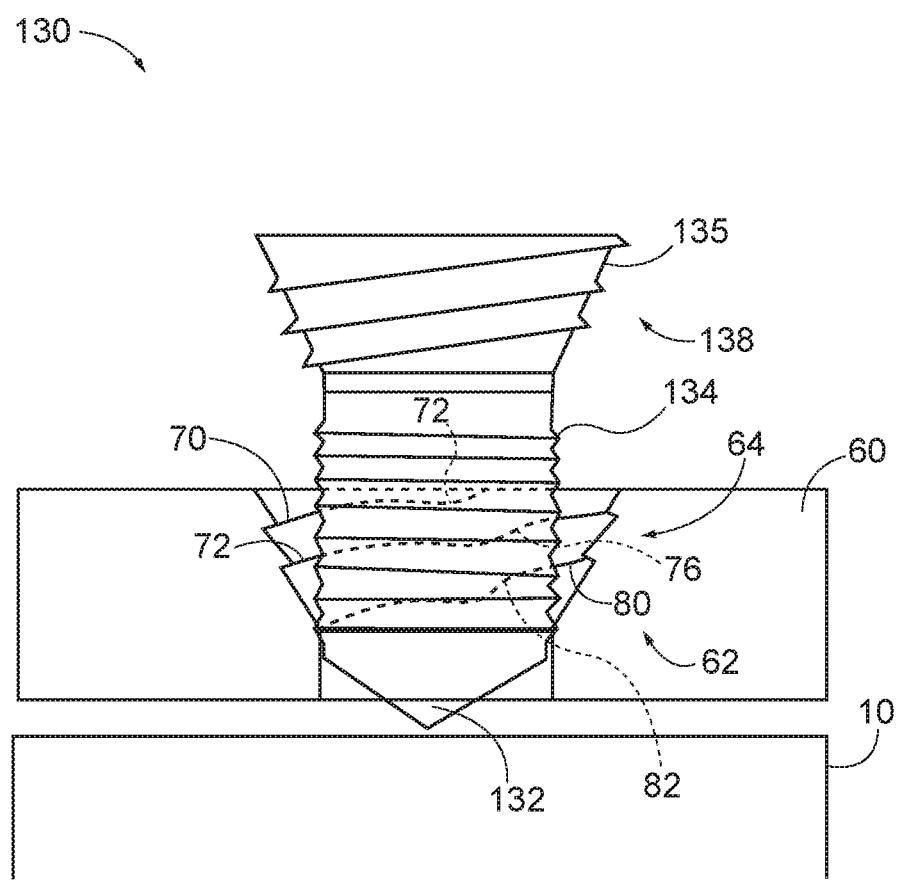
FIG. 7B depicts a cross-sectional front view of the bone screw and bone plate of FIG. 7A, where the bone screw is initially inserted into the bone plate to make initial contact with the bone of FIG. 1.
Figure 7C:
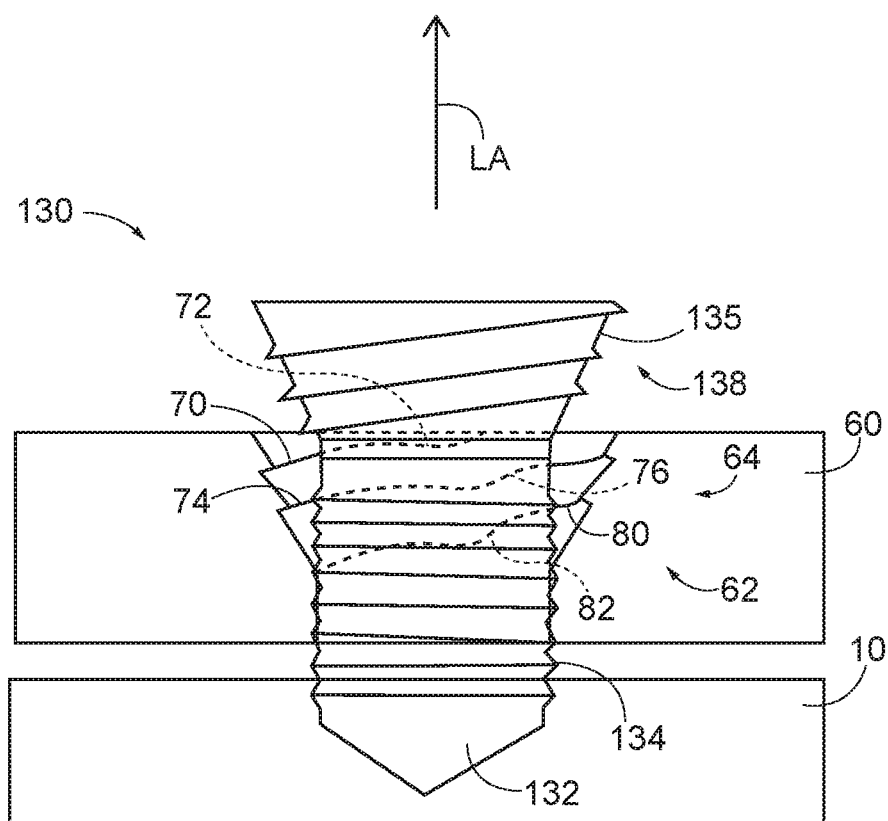
FIG. 7C depicts a cross-sectional front view of the bone screw and bone plate of FIG. 7A, where the bone screw is further inserted into the bone plate and the bone of FIG. 1.
Figure 7D:
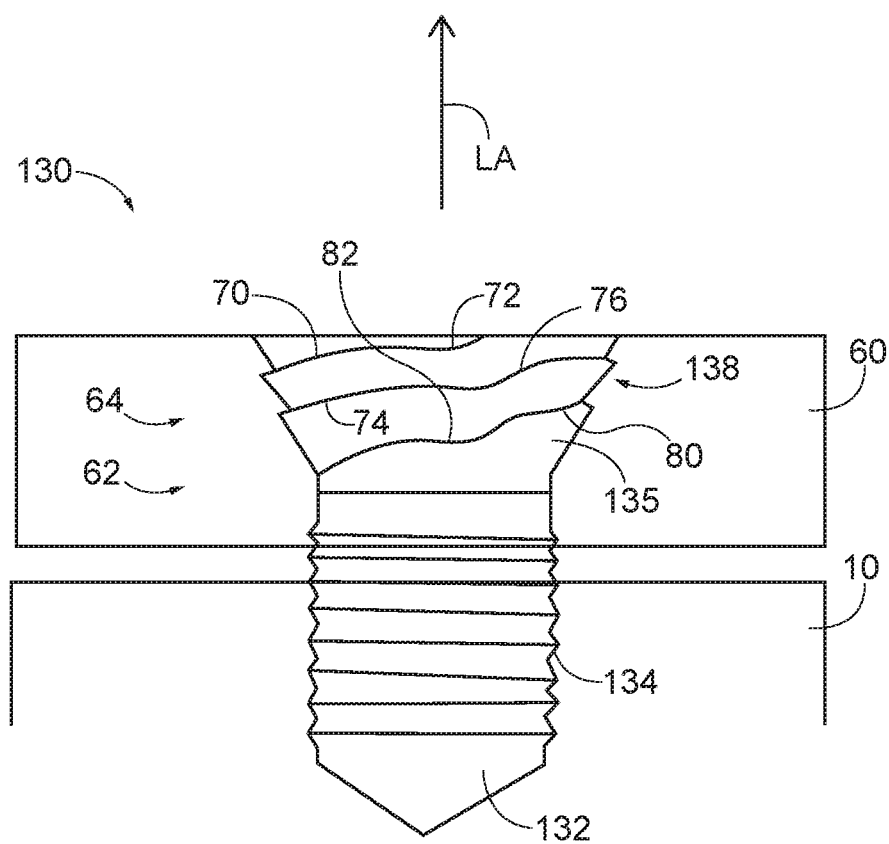
FIG. 7D depicts a cross-sectional front view of the bone screw and bone plate of FIG. 7A, where the bone screw is coupled with the bone plate and fully inserted into the bone of FIG. 1.

FIGS. 7A-7D show an exemplary use of bone screw (130) and bone plate (60). First, the operator may place bone plate (60) at a sufficient location relative to bone (10). Next, the operator may align bone screw (130) relative to bone plate (60) such that self-tapping flutes (132) are directly adjacent to threaded through hole (62). Next, as shown in FIG. 7B, the operator may insert self-tapping flutes (132) through threaded through hole (62) until self-tapping flutes (132) contact an outer surface of bone (10). Next, as shown in FIG. 7C, the operator may drive rotation of bone screw (130) about its own longitudinal axis (LA) via a driving mechanism and drive recess (not shown) such that self-tapping flutes (132) begin to penetrate bone (10). Next, as shown in FIG. 7D the operator may further drive rotation of bone screw (130) about its own longitudinal axis (LA) such that first threaded portion (134) suitably engages bone (10), and such that deformable locking threaded portion (138) deforms to the profile of irregular female threading (64) in accordance with the description above.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A bone screw assembly, comprising: (a) a first body, wherein the first body comprises: (i) a proximal portion, (ii) a distal portion, wherein the first body extends from the proximal portion toward the distal portion along a longitudinal axis, wherein the distal portion is configured to pierce bone in response to rotation of the first body about the longitudinal axis, and (iii) a first threaded section, wherein the first threaded section is configured to engage bone; (b) a second body, wherein the second body defines a through hole dimensioned to receive the distal portion of the first body; and (c) a thread locking assembly configured to couple the first body with the second body, wherein the thread locking assembly comprise locking assembly comprises: (i) a first threaded locking section associated with the proximal portion of the first body, (ii) a second threaded locking section associated with the through hole of the second body, wherein the first threaded locking section is configured rotate relative to the second threaded locking section in order to mesh with the second thread locking section, wherein either the first threaded locking section or the second threaded locking section is configured to deform the other in response to rotation of the first threaded locking section relative to the second threaded locking section.

Example 2

The bone screw assembly of Example 1, wherein the second threaded locking section is configured to deform the first threaded locking section in response to rotation of the first threaded locking section relative to the second threaded locking section.

Example 3

The bone screw assembly of Example 2, wherein the second threaded locking section comprises a non-uniform wave configured to deform the first threaded locking section.

Example 4

The bone screw assembly of Example 3, wherein the second threaded locking section comprises a first helix angle, wherein the non-uniform wave comprises a deviated helix angle.

Example 5

The bone screw assembly of any one or more of Examples 2 through 4, wherein the second threaded locking section comprises a first portion and a second portion continuously connected with each other.

Example 6

The bone screw assembly of Example 5, wherein the first portion comprises a first pitch, wherein the second portion comprises a second pitch, wherein the first pitch is different than the second pitch.

Example 7

The bone screw assembly of Example 6, wherein the first portion of the second threaded locking section is proximal relative to the second portion of the second threaded locking section.

Example 8

The bone screw assembly of Example 7, wherein the first threaded locking section is configured to traverse the first portion of the second threaded locking section without deforming, wherein the first threaded locking section is configured to traverse the second pitch while deforming.

Example 9

The bone screw assembly of any one or more of Examples 5 through 8, wherein the first portion comprises a first helix angle, wherein the second portion comprises a second helix angle.

Example 10

The bone screw assembly of Example 9, wherein the first threaded locking section is configured to traverse the first portion of the second threaded locking section without deforming, wherein the first threaded locking section is configured to traverse the second pitch while deforming.

Example 11

The bone screw assembly of any one or more of Examples 5 through 10, wherein the first portion comprises a first thread angle, wherein the second portion comprises a second thread angle, wherein the second thread angle is different than the first thread angle.

Example 12

The bone screw assembly of any one or more of Examples 5 through 11, wherein the first portion comprises a first crest-root distance, wherein the second portion comprises a second crest-root distance, wherein the second crest-root distance is different than the first crest-root distance.

Example 13

The bone screw assembly of any one or more of Examples 1 through 12, wherein the second body comprises a prosthesis.

Example 14

The bone screw assembly of Example 13, wherein the prosthesis comprises an acetabular component of a hip replacement assembly.

Example 15

The bone screw assembly of any one or more of Examples 1 through 14, wherein the proximal portion of the first body defines a drive recess.

Example 16

The bone screw assembly of any one or more of Examples 1 through 15, wherein the distal portion of the first body comprises a self-tapping flute.

Example 17

The bone screw assembly of any one or more of Examples 1 through 16, wherein the second body comprises a bone plate.

Example 18

A bone screw assembly, comprising: (a) a first body, wherein the first body comprises: (i) a proximal portion, (ii) a distal portion, wherein the first body extends from the proximal portion toward the distal portion along a longitudinal axis, wherein the distal portion is configured to pierce bone in response to rotation of the first body about the longitudinal axis, and (iii) a first threaded section, wherein the first threaded section is configured to engage bone; (b) a second body, wherein the second body defines a through hole dimensioned to receive the distal portion of the first body; and (c) a thread locking assembly configured to couple the first body with the second body, wherein the thread locking assembly comprise locking assembly comprises: (i) a first threaded locking section associated with the proximal portion of the first body, (ii) a second threaded locking section associated with the through hole of the second body, wherein the first threaded locking section is configured rotate relative to the second threaded locking section in order to mesh with the second thread locking section, wherein the second threaded locking section comprises an irregular female threading, wherein either the first threaded locking section is configured to deform the second threaded locking section or the second threaded locking section is configured to deform the first threaded locking section as the first threaded locking section rotates relative to the second threaded locking section.

Example 19

The bone screw assembly of Example 18, wherein the irregular female threading comprises a wave pattern.

Example 20

A bone screw assembly, comprising: (a) a first body, wherein the first body comprises a first threaded section, wherein the first threaded section is configured to engage bone; (b) a second body, wherein the second body defines a through hole dimensioned to receive a portion of the first body, wherein the through hole extends along a longitudinal axis; and (c) a thread locking assembly configured to couple the first body with the second body, wherein the thread locking assembly comprise locking assembly comprises: (i) a first threaded locking section associated with the proximal portion of the first body, (ii) a second threaded locking section associated with the through hole of the second body, wherein the first threaded locking section is configured rotate relative to the second threaded locking section in order to mesh with the second thread locking section, wherein the second threaded locking section is not axisymmetric about the longitudinal axis.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A bone screw assembly, comprising:
   (a) a first body, wherein the first body comprises:
      (i) a proximal portion,
      (ii) a distal portion, wherein the first body extends from the proximal portion toward the distal portion along a longitudinal axis, wherein the distal portion is configured to pierce bone in response to rotation of the first body about the longitudinal axis, and
      (iii) a first threaded section, wherein the first threaded section is configured to engage bone;
   (b) a second body, wherein the second body defines a through hole dimensioned to receive the distal portion of the first body; and
   (c) a thread locking assembly configured to couple the first body with the second body, wherein the thread locking assembly comprises:
      (i) a first threaded locking section associated with the proximal portion of the first body,
      (ii) a second threaded locking section associated with the through hole of the second body, wherein the second threaded locking section comprises a first portion and a second portion continuously connected with each other, wherein the first portion comprises a first thread angle, wherein the second portion comprises a second thread angle, wherein the second thread angle is different than the first thread angle, wherein the first threaded locking section is configured rotate relative to the second threaded locking section in order to mesh with the second thread locking section, wherein either the first threaded locking section or the second threaded locking section is configured to deform the other in response to rotation of the first threaded locking section relative to the second threaded locking section.

2. The bone screw assembly of claim 1, wherein the second threaded locking section is configured to deform the first threaded locking section in response to rotation of the first threaded locking section relative to the second threaded locking section.

3. The bone screw assembly of claim 2, wherein the second threaded locking section comprises a non-uniform wave configured to deform the first threaded locking section.

4. The bone screw assembly of claim 3, wherein the second threaded locking section comprises a first helix angle, wherein the non-uniform wave comprises a deviated helix angle.

5. The bone screw assembly of claim 1, wherein the first portion comprises a first pitch, wherein the second portion comprises a second pitch, wherein the first pitch is different than the second pitch.

6. The bone screw assembly of claim 5, wherein the first portion of the second threaded locking section is proximal relative to the second portion of the second threaded locking section.

7. The bone screw assembly of claim 6, wherein the first threaded locking section is configured to traverse the first portion of the second threaded locking section without deforming, wherein the first threaded locking section is configured to traverse the second pitch while deforming.

8. The bone screw assembly of claim 1, wherein the first portion comprises a first helix angle, wherein the second portion comprises a second helix angle.

9. The bone screw assembly of claim 8, wherein the first threaded locking section is configured to traverse the first portion of the second threaded locking section without deforming, wherein the first threaded locking section is configured to traverse the second portion while deforming.

10. The bone screw assembly of claim 1, wherein the first portion comprises a first crest-root distance, wherein the second portion comprises a second crest-root distance, wherein the second crest-root distance is different than the first crest-root distance.

11. The bone screw assembly of claim 1, wherein the second body comprises a prosthesis.

12. The bone screw assembly of claim 11, wherein the prosthesis comprises an acetabular component of a hip replacement assembly.

13. The bone screw assembly of claim 1, wherein the proximal portion of the first body defines a drive recess.

14. The bone screw assembly of claim 1, wherein the distal portion of the first body comprises a self-tapping flute.

15. The bone screw assembly of claim 1, wherein the second body comprises a bone plate.

16. A bone screw assembly, comprising:
   (a) a first body, wherein the first body comprises:
      (i) a proximal portion,
      (ii) a distal portion, wherein the first body extends from the proximal portion toward the distal portion along a longitudinal axis, wherein the distal portion is configured to pierce bone in response to rotation of the first body about the longitudinal axis, and
      (iii) a first threaded section, wherein the first threaded section is configured to engage bone;
   (b) a second body, wherein the second body defines a through hole dimensioned to receive the distal portion of the first body; and
   (c) a thread locking assembly configured to couple the first body with the second body, wherein the thread locking assembly comprises:
      (i) a first threaded locking section associated with the proximal portion of the first body,
      (ii) a second threaded locking section associated with the through hole of the second body, wherein the first threaded locking section is configured rotate relative to the second threaded locking section in order to mesh with the second thread locking section, wherein the second threaded locking section comprises an irregular female threading, wherein the irregular female threading further comprises a first portion and a second portion continuously connected with the first portion, wherein the first portion comprises a first thread angle, wherein the second portion comprises a second thread angle that is different from the first thread angle, wherein the second threaded locking section is configured to deform the first threaded locking section as the first threaded locking section rotates relative to the second threaded locking section via engagement between the irregular female threading and the first threaded locking section while the through hole is coaxially aligned with the longitudinal axis of the first body.

17. The bone screw assembly of claim 16, wherein the irregular female threading comprises a wave pattern.

18. A bone screw assembly, comprising:
(a) a first body, wherein the first body comprises a first threaded section, wherein the first threaded section is configured to engage bone;
(b) a second body, wherein the second body defines a through hole dimensioned to receive a portion of the first body, wherein the through hole extends along a longitudinal axis; and
(c) a thread locking assembly configured to couple the first body with the second body, wherein the thread locking assembly comprises:
  (i) a first threaded locking section associated with the first body,
  (ii) a second threaded locking section associated with the through hole of the second body, wherein the first threaded locking section is configured rotate relative to the second threaded locking section in order to mesh with the second threaded locking section such that the second threaded locking section is configured to thereby deform the first threaded locking section while the first body is coaxially aligned with the longitudinal axis of the through hole, wherein the second threaded locking section is not axisymmetric about the longitudinal axis, wherein the second threaded locking section comprises a first portion and a second portion continuously connected with each other, wherein the first portion comprises a first thread angle, wherein the second portion comprises a second thread angle, wherein the second thread angle is different than the first thread angle.

* * * * *